United States Patent [19]
Benton

[11] Patent Number: 5,833,824
[45] Date of Patent: Nov. 10, 1998

[54] DORSAL SUBSTRATE GUARDED ISFET SENSOR

[75] Inventor: Barry W. Benton, Orange, Calif.

[73] Assignee: Rosemount Analytical Inc., La Habra, Calif.

[21] Appl. No.: 751,085

[22] Filed: Nov. 15, 1996

[51] Int. Cl.⁶ .......................... G01N 27/26; H01L 27/14; H01L 29/82; H01L 29/84
[52] U.S. Cl. .......................... 204/416; 204/417; 257/414; 257/429; 257/680; 438/49; 438/126
[58] Field of Search .................. 204/416–419; 257/414, 428–430, 680; 438/49, 126

[56] References Cited

U.S. PATENT DOCUMENTS

| | | | |
|---|---|---|---|
| 4,020,830 | 5/1977 | Johnson et al. | 128/2 E |
| 4,086,642 | 4/1978 | Yoshida et al. | 361/91 |
| 4,157,611 | 6/1979 | Ohwaki et al. | 29/588 |
| 4,218,298 | 8/1980 | Shimada et al. | 204/195 |
| 4,354,308 | 10/1982 | Shimada et al. | 29/571 |
| 4,397,714 | 8/1983 | Janata et al. | 204/1 T |
| 4,411,741 | 10/1983 | Janata | 204/1 T |
| 4,505,799 | 3/1985 | Baxter | 204/416 |
| 4,514,263 | 4/1985 | Janata | 204/1 T |
| 4,514,646 | 4/1985 | Ando et al. | 307/200 |
| 4,534,825 | 8/1985 | Koning et al. | 156/644 |
| 4,589,970 | 5/1986 | Ligtenberg et al. | 204/406 |
| 4,657,658 | 4/1987 | Sibbald | 204/406 |
| 4,816,118 | 3/1989 | Oyama et al. | 204/418 |
| 4,851,104 | 7/1989 | Connery et al. | 204/406 |
| 4,874,499 | 10/1989 | Smith et al. | 204/403 |
| 4,903,099 | 2/1990 | Sekiguchi et al. | 257/414 |
| 4,921,591 | 5/1990 | Mochizuki et al. | 204/412 |
| 4,961,833 | 10/1990 | Sakai et al. | 204/406 |
| 5,025,298 | 6/1991 | Fay et al. | 357/41 |
| 5,068,205 | 11/1991 | Baxter et al. | 437/405 |
| 5,250,168 | 10/1993 | Tsukada et al. | 204/416 |
| 5,293,069 | 3/1994 | Kato et al. | 257/698 |
| 5,311,042 | 5/1994 | Anceau | 257/173 |
| 5,407,854 | 4/1995 | Baxter et al. | 437/54 |
| 5,414,284 | 5/1995 | Baxter et al. | 257/253 |
| 5,478,526 | 12/1995 | Sakai et al. | 422/81 |

FOREIGN PATENT DOCUMENTS

| | | |
|---|---|---|
| 0 043 284 | 6/1982 | European Pat. Off. |
| 0 489 601 A2 | 6/1991 | European Pat. Off. |
| 54-140881 | 1/1979 | Japan . |
| 2 060 255 | 4/1981 | United Kingdom . |

OTHER PUBLICATIONS

Hon–Sum Wong and Marvin H. White, "A CMOS–Integrated " ISFET–Operational Amplifier Chemical Sensor Employing Differntial Sensing, *IEEE Transactions on Electron Devices*, vol. 36, No. 3, Mar. 1989, pp. 479–487.

Thesis of Rosemary L. Smith entitled, "Ion–Sensitive Field Effect Transistors With Polysilicon Gates,", Department of Engineering, doctoral dissertation, University of Utah, Jun. 1982.

*Primary Examiner*—Mahshid D. Saadat
*Assistant Examiner*—Allan R. Wilson
*Attorney, Agent, or Firm*—Westman, Champlin & Kelly, P.A.

[57] ABSTRACT

An Ion-sensitive Field Effect Transistor (ISFET) sensor for sensing ion activity of a solution includes a substrate and an ISFET semiconductor die. The substrate has front surface exposed to the solution, a back surface opposite to the front surface and aperture extending between the front and back surfaces. The ISPET semiconductor die has an ion-sensitive surface with a gate region. The ion-sensitive surface is mounted to the back surface such that the gate region is exposed to the solution through the aperture.

27 Claims, 16 Drawing Sheets

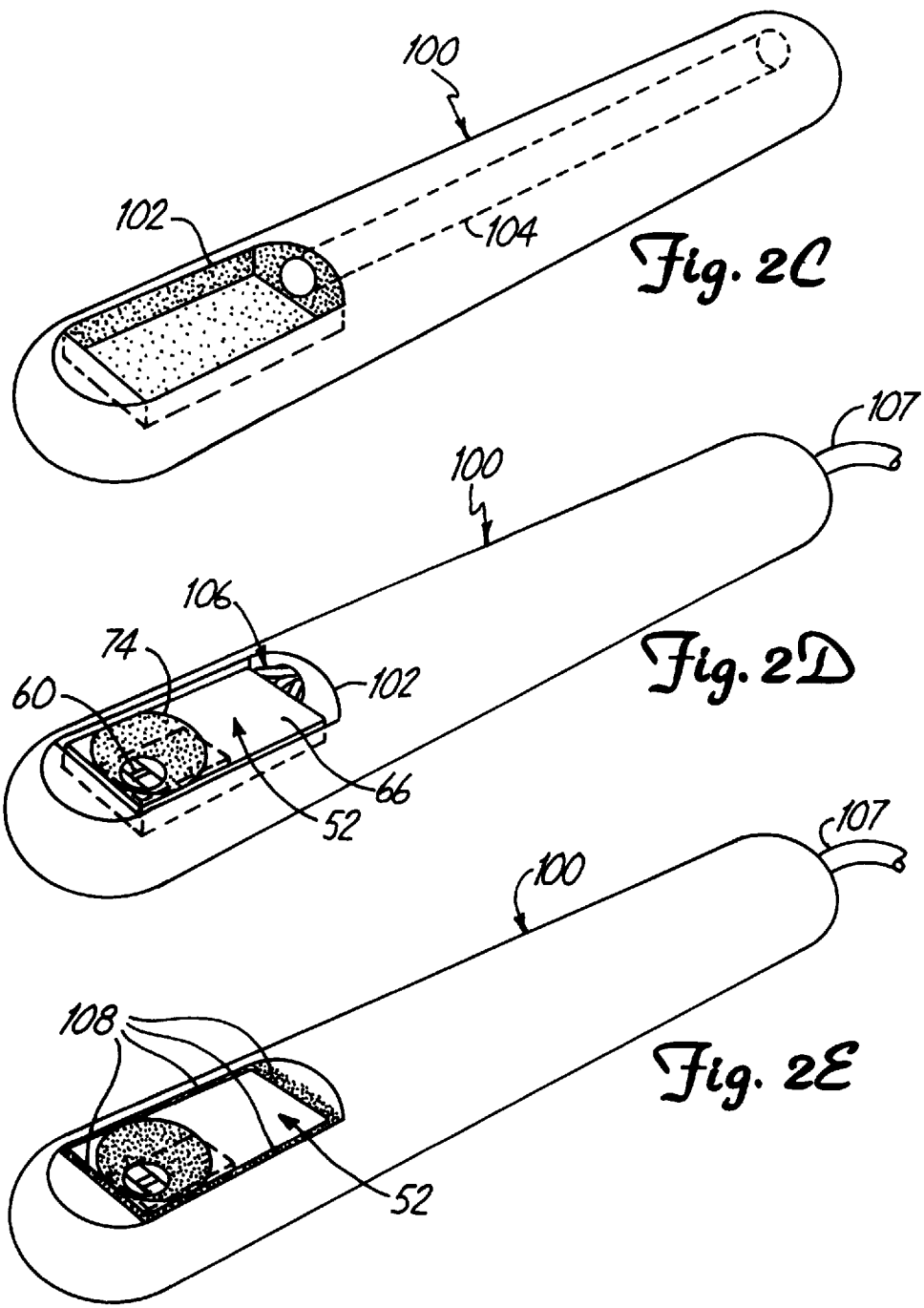

5,833,824

DORSAL SUBSTRATE GUARDED ISFET SENSOR

BACKGROUND OF THE INVENTION

The present invention relates to an Ion Sensitive Field Effect Transistor (ISFET) sensor for sensing ion activity of a sample solution and, more particularly, to an ISFET sensor mounted behind a substrate with respect to the sample solution.

An ISFET is similar to a Metal Oxide Semiconductor Field Effect Transistor (MOSFET), but does not have a conductive gate terminal. Instead, an ion-sensitive membrane is placed over the gate or channel region and is exposed to a sample solution. The remainder of the ISFET device is encapsulated. The lead that would be attached to the gate terminal of a MOSFET is attached to a reference electrode. The reference electrode is separated from the ion-sensitive membrane by the solution. The ion-sensitive membrane modulates the gate charge, and thus the potential difference between the gate and the reference electrode, as a function of the ion concentration in the sample solution. One or more of the operating characteristics of the ISFET are then measured and used to calculate the ion concentration.

ISFETs are typically fabricated with other devices, such as temperature transducers, temperature compensation diodes or exposed metallic areas, on a common semiconductor chip. This chip is referred to as an ISFET "die". The fragile ISFET die is mounted to a larger support structure which carries conductors for electrical connection with the ISFET die. This support structure is referred to as a "substrate". The die and substrate are then mounted within a larger sensor support structure and encapsulated with an epoxy, leaving only the ion-sensitive membrane at the gate region exposed to the solution. In a traditional ISFET sensor, the ISFET die is mounted to the front surface of the substrate such that the ion sensitive membrane on the die faces away from the substrate and toward the sample solution.

This structure has been susceptible to degradation of the ISFET sensor by the solution in harsh environments, such as high temperature or highly corrosive environments. With common ISFET sensor fabrication techniques, epoxy sealing causes three basic problems. First, the conductors on the ISFET die are connected to corresponding conductors on the substrate by fine metal wire loops. The ISFET die and the related wire connections are then covered with a large drop of epoxy. In the extremes of service temperature, these fine wires break due to a mismatch in the thermal expansion of the epoxy relative to the thermal expansion of the ISFET die, the substrate or the wires. Wire breakage results in sensor failure.

Second, since the gate region must be exposed to the solution, the epoxy is necessarily thin around the gate region while the area covered by the epoxy is relatively large. The thin epoxy is susceptible to ionic permeation or leakage of the sample solution, hydration of the epoxy by the solution and chemical attack of the epoxy, which results in erroneous signal output and corrosion damage to the wires and other electrical connections to the ISFET die.

Even if the leakage or permeation causes no direct physical damage, the electrolytic reaction between the electrical conductors and the solution alters the measurement signals generated by the ISFET and the sensor becomes unusable. Also, simple hydration of the epoxy by the solution will, over a longer time, produce an electrolyte from epoxy impurities, giving the same result.

Third, the bond between the epoxy and the ISFET die surface is slowly broken around the gate area by the solution. The shape of the epoxy drop allows the edge of the epoxy to rise from the ISFET die surface at the broken bond, which exposes more of the bond to the solution. The hydration of the epoxy also causes the extremely thin section around the gate to expand, further increasing bond damage.

Attempts have been made to hermetically seal the ISFET die. However, existing hermetically sealed ISFET sensors are prone to abrasion because there is no epoxy crater to shield the ion-sensitive membrane at the gate region from the flowing sample solution. The ion-sensitive membrane is typically only about 500 Angstroms thick.

SUMMARY OF THE INVENTION

The Ion Sensitive Field Effect Transistor (ISFET) sensor of the present invention includes a first substrate and an ISFET semiconductor die. The first substrate has a front surface exposed to the solution, a back surface opposite to the front surface and an aperture extending between the front and back surfaces. The ISFET semiconductor die has an ion-sensitive surface with a gate region. The ion-sensitive surface is mounted to the back surface such that the gate region is exposed to the solution through the aperture.

In one embodiment, the ISFET sensor further includes a sealing ring, such as a thermal-pressure gold bond, positioned between the first substrate and the ISFET semiconductor die and surrounding the aperture. The sealing ring seals the die from the solution except at the gate region. The sealing ring may be mounted to the first substrate or the ISFET semiconductor die or may include two sealing rings which are mounted to the first substrate and the ISFET semiconductor die and then bonded together. The substrate and die are then mounted within a larger support structure or sensor housing and sealed with a condensation polymer such as Parylene. In an alternative embodiment, the first substrate, the ISFET semiconductor die and the sensor housing are all sealed with a conductive polymer in a single fabrication step to form a continuous seal.

In another embodiment, the ISFET sensor further includes a second substrate bonded to the back surface of the first substrate and extending around a periphery of the ISFET semiconductor die such that the die is enclosed and sealed by the first and second substrates.

BRIEF DESCRIPTION OF THE DRAWINGS

FIGS. 2A–2E are perspective views of an ISFET sensor according to one embodiment of the present invention.

DETAILED DESCRIPTION OF THE PREFERRED EMBODIMENTS

The Ion Sensitive Field Effect Transistor (ISFET) sensor of the present invention includes an ISFET semiconductor die which is mounted to the back surface of a substrate, with an ion sensitive membrane on the die being exposed to a sample solution through an aperture in the substrate. The substrate is formed of an impenetrable, abrasion resistant material which covers the entire ISFET die, except for the gate region. This limits damage from the solution to a thin band of sealing material adjacent the aperture, between the die and the substrate, which seals the gate region from the rest of the ISFET die. The substrate also prevents the sealing material from lifting off of the die surface. Because the ion sensitive surface of the die is bonded directly to the substrate, electrical connections between the die and the substrate can be made directly without requiring wire loops to extend through an epoxy seal, which reduces susceptibility to thermal expansion breakage. These advantages greatly extend operational life of the ISFET sensor of the present invention.

Figure 1A:
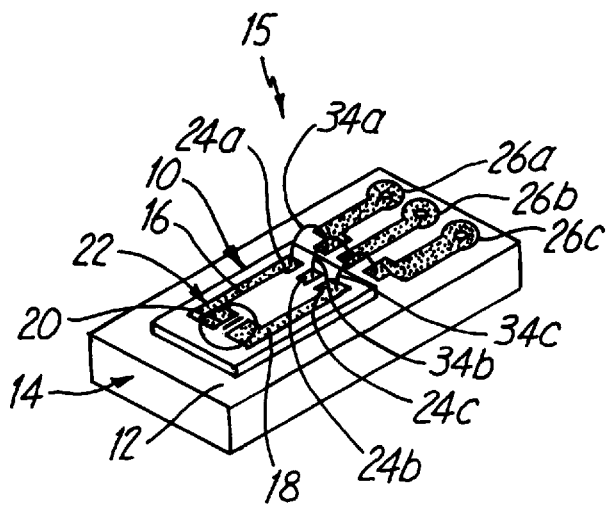
FIGS. 1A–1C are perspective views of an ISFET sensor of the prior art.
Figure 1B:
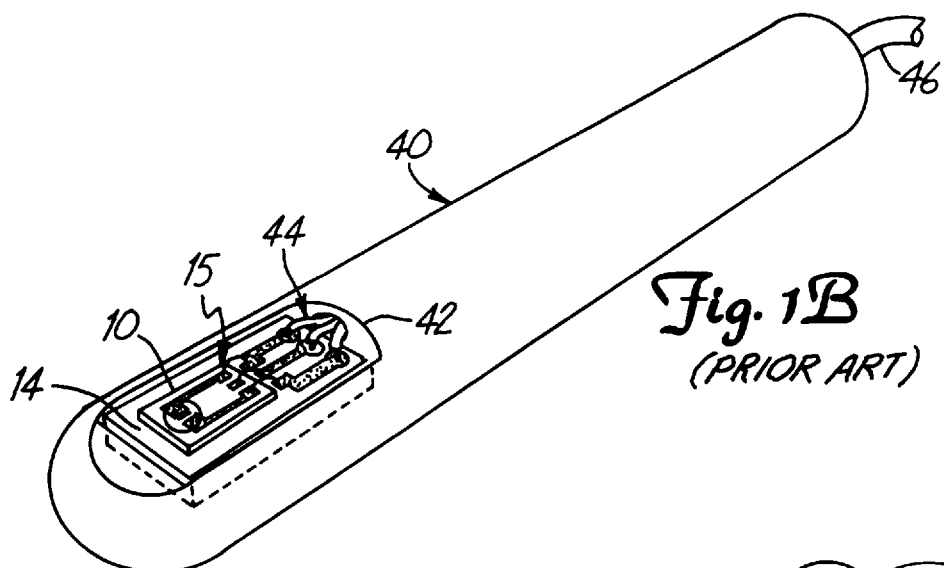
Figure 1C:
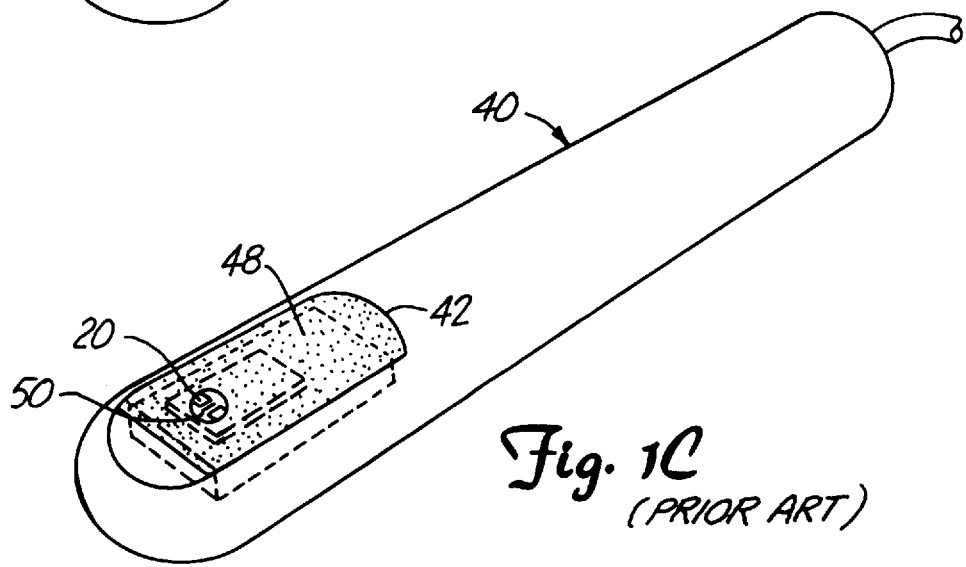

FIGS. 1A–1C illustrate an ISFET sensor of the prior art. In FIG. 1A, an ISFET semiconductor die 10 is bonded to a front surface 12 of a substrate 14 to form an ISFET sensor assembly 15. This bond is typically made with an epoxy. The ISFET on die 10 is formed of a source 16, a drain 18 and a gate 20. An ion sensitive membrane 22 is applied over the gate region, which faces away from substrate 14 tor contact with the sample solution (not shown). Ion-sensitive membrane 22 modulates the gate charge as function of the ion concentration of the sample solution. Source 16 and drain 18 are electrically coupled to die bonding pads 24a and 24c, respectively. Die bonding pad 24b is coupled to the semiconductor body of die 10. Substrate 14 includes substrate bonding pads 26a–26c which are electrically coupled to die bonding pads 24a–24c through wire loops 34a–34c.

Once ISFET die 10 and substrate 14 are bonded together to form assembly 15, the assembly is mounted within sensor housing 40, as shown in FIG. 1B. Sensor housing 40 includes an aperture 42 for receiving assembly 15 and an internal cavity which carries sensor wiring 44. Sensor wiring 44 is attached to substrate bonding pads 26a–26c. Sensor housing 40 may also carry a preamplifier or other circuitry for receiving measurements from ISFET die 10 over wiring 44 and for transmitting the measurements over a sensor cable 46.

As shown in FIG. 1C, ISFET die 10 and substrate 14 are sealed within aperture 42 by a large drop of epoxy 48. Epoxy 48 includes an aperture 50 through which the gate region 20 of ISFET die 10 remains exposed to the solution. Since the gate region must remain exposed, epoxy 48 is necessarily thin, while the area covered by the epoxy is relatively large. The shape of the epoxy drop allows the bond between epoxy 48 and the surface of ISFET die 10 to break slowly, which allows the edge of the epoxy to rise from the surface of ISFET die 10 at the broken bond and exposes more of the bond to the solution. Hydration of epoxy 48 also causes the extremely thin section of epoxy around the gate region to expand, further increasing bond damage. This results in leakage and permeation of the sample solution onto the die surface and into sensor housing 40, which causes corrosive damage and an erroneous signal output of the sensor. Also, the high thermal coefficient of expansion of epoxy 48, relative to substrate 14, ISFET die 10 and wires 34a–34c and 44 stresses and breaks the wire loops at higher operating temperatures, resulting in sensor failure.

Figure 2A:
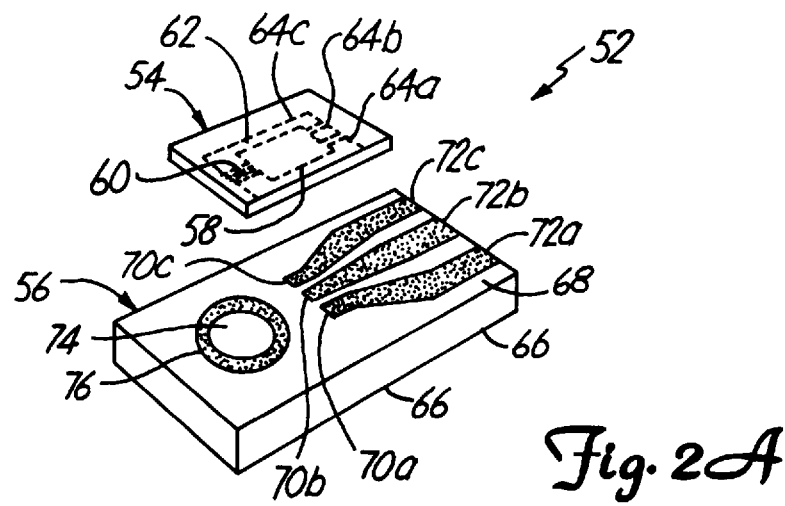
Figure 2B:
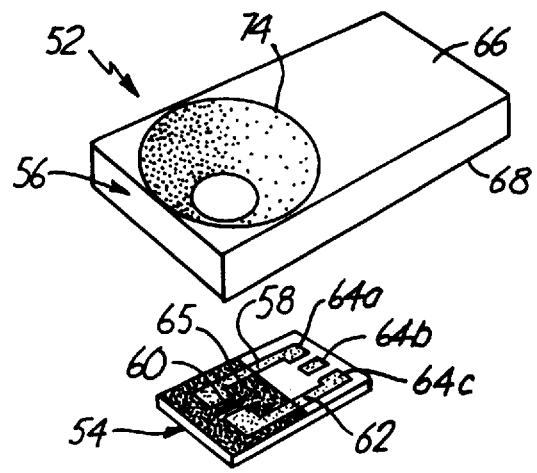

FIGS. 2A–2E illustrate an ISFET sensor assembly 52 according to one embodiment of the present invention. Referring to FIGS. 2A and 2B, which show sensor assembly 52 from opposite surfaces, ISFET sensor assembly 52 includes ISFET die 54 and substrate 56. ISFET die 54 is flipped over such that its ion-sensitive surface faces substrate 56. ISFET die 54 includes source 58, gate 60 and drain 62. Source 58 and drain 62 are coupled to die bonding pads 64a and 64c. Die bonding pad 64b is coupled to the semiconductor substrate of ISFET die 54. An ion-sensitive membrane 65 is applied over the gate region of ISFET die 64. Ion-sensitive membrane 65 is formed of alumina, tantalum pentoxide or silicon nitride, for example. Other ion-sensitive materials can also be used. A thin layer 144, 172 of metal (shown in FIGS. 6C and 7) may be formed over ion-sensitive membrane 65, except along gate 60, to provide protection from light and an electrical ground to the solution. In one embodiment, the layer is formed of platinum. However, other materials can also be used, such as nickel, titanium, tantalum, gold, and palladium silver. The metal layer can also be used as an oxide reduction potential (ORP) membrane for measuring oxide or reduction potential.

Substrate 56 includes a front surface 66 and a back surface 68. Substrate bonding pads 70a–70c are formed on back surface 68 and are electrically coupled to substrate solder pads 72a–72c through conductive traces. The conductive traces can include metallized layers, conductive inks, conductive polymers or other non-metallic conductors, as desired. The conductive traces on substrate 56 can be arranged for a pin array attachment, a printed circuit board attachment or a wire lead attachment for example. In addition, substrate 56 can include additional selective metallization for bonding, sealing, or vapor barrier formation.

When ISFET die 54 is mounted to substrate 56, die bonding pads 64a–64c directly abut substrate bonding pads 70a–70c and are bonded together with an electrically conductive adhesive or solder, which makes the desired electrical connections and secures the die to the substrate.

Substrate 56 further includes an aperture 74 which exposes gate region 60 of ISFET die 54 to the sample solution when die 54 is mounted to substrate 56. Aperture 74 is formed with angled side walls such that the aperture has a larger diameter at front surface 66 than at back surface 68. In alternative embodiments, aperture 74 can have side walls which are vertical, curved, angled or otherwise modified from either surface. Substrate aperture 74 is circular, but could also have a square, rectangular, oval or other geometry.

A substrate sealing ring 76 is applied to substrate 56 around aperture 74 for providing a seal which prevents leakage of the sample solution between the die and the substrate. Substrate sealing ring 76 may seal directly to ISFET die 54 or to a corresponding sealing ring on the die. The sealing material can have the shape of a ring or any other suitable shape, such as a layer, which seals ISFET die 54 with respect to substrate aperture 74, except at the gate region. Substrate sealing ring 76 can be formed in place during fabrication of the substrate or added during the subassembly as a preformed part which is inserted between the substrate and the die when the die is mounted to the substrate. In a preferred embodiment, sealing ring 76 is a gold ring which is thermal-pressure bonded to die 54 or to a corresponding gold ring on die 54. Other metals, alloys, glasses or polymers may also be used to achieve chemical resistance, structural support, insulation, surface bonding, vapor barrier formation or circuit metallization properties that are suitable for the particular application in which the sensor is used. For example, the sealing ring can be formed of metals such as platinum, nickel, titanium, tantalum, and palladium silver.

In a preferred embodiment, substrate 56 is formed of alumina. However, other ceramics, metals, glasses and plastics may also be used to provide particular chemical resistance, structural support, insulation, surface bonding, vapor barrier or circuit metallization properties which may be desired for the embodiment in which the sensor is used. Also, substrate 56 can have various geometries. For example, the side edges of substrate 56 can be vertical, curved, angled or another shape. The corners of substrate 56 can be square, round or truncated for example. Substrate 56 can have a plan form, as view from front surface 66 or back surface 68, which is square, rectangular, round, oval or another geometry or a combination of geometries.

FIG. 2C is a perspective view of a sensor housing 100 for holding the ISFET sensor assembly 52 Sensor housing 100 includes a recess or aperture 102 for receiving assembly 52 and a lumen 104 for carrying wires which communicate with ISFET die 54. In FIG. 2D, the ISFET sensor assembly 52 is inserted into aperture 102, with front surface 66 of substrate 56 facing an exterior of sensor housing 100. Wires 106 are soldered to substrate wire solder pads 72a–72c (shown in FIG. 2A) and threaded through lumen 104 for coupling to sensor cable 107.

The ISFET sensor assembly 52 is then sealed within sensor housing 100 with a sealant 108, as shown in FIG. 2E. In a preferred embodiment, the ISFET gate area is masked and the sensor is placed into a Parylene condensation chamber. Parylene monomers "leak" into the sensor through any available openings. As the gaseous monomers condense into a polymer on the sensor surfaces, the polymer thickness increases to a point at which all gaps are closed and sealed by the condensed polymer.

In an alternative embodiment, the gate area remains unmasked. Any condensed Parylene polymer on the gate area is later vaporized with a laser, for example. In another alternative embodiment, sealing ring 76 is eliminated and replaced with a condensed Parylene polymer seal. In this embodiment, ISFET die 54 is fixtured onto substrate 56 so that there is a small gap between the die and the substrate about substrate aperture 74. The Parylene monomers condense within the gap to form the desired seal around substrate aperture 74. This allows the use of Parylene condensation to seal all components at once, from ISFET die 54 to sensor housing 100, yielding one continuous, uninterrupted sample solution resistant surface. Other condensation polymers, metal depositions, metals, alloys, glasses or polymers can also be used for sealing ISFET die 54 and substrate 56 to sensor housing 100 for providing desired chemical resistance, structural support, insulation, surface bonding or vapor barrier properties.

Figure 3A:
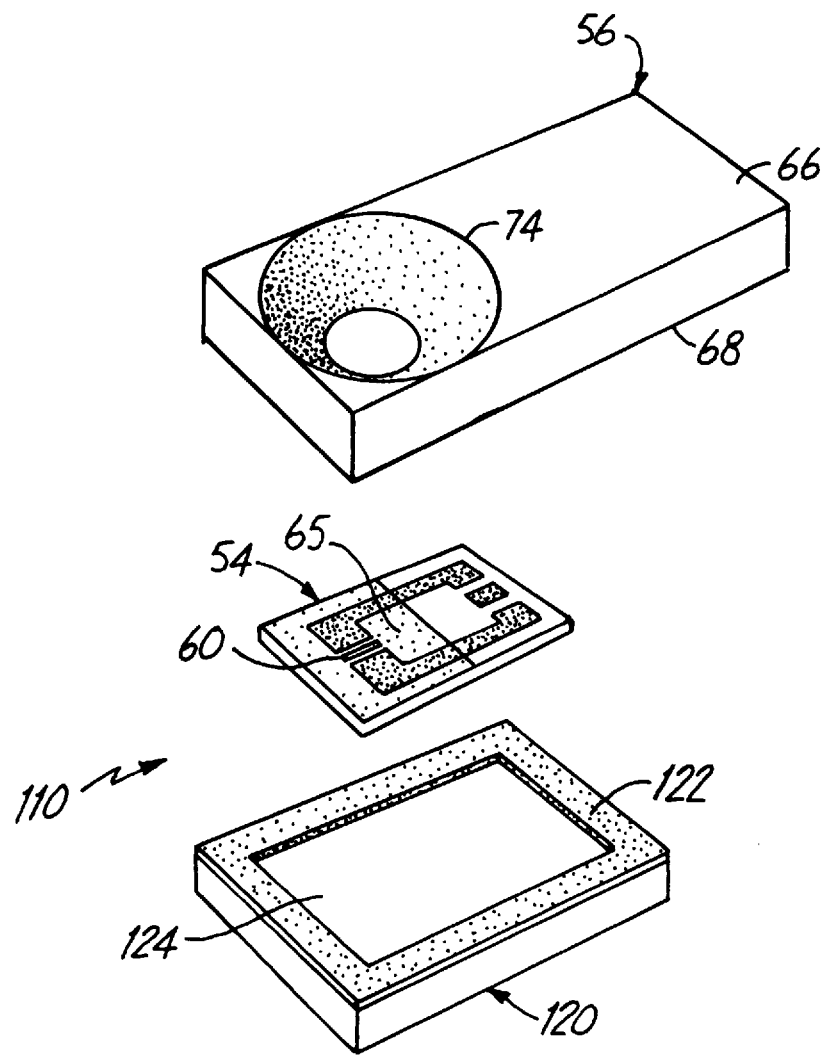
FIGS. 3A–3C are perspective views of an ISFET sensor having a second substrate according to an alternative embodiment of the present invention.
Figure 3B:
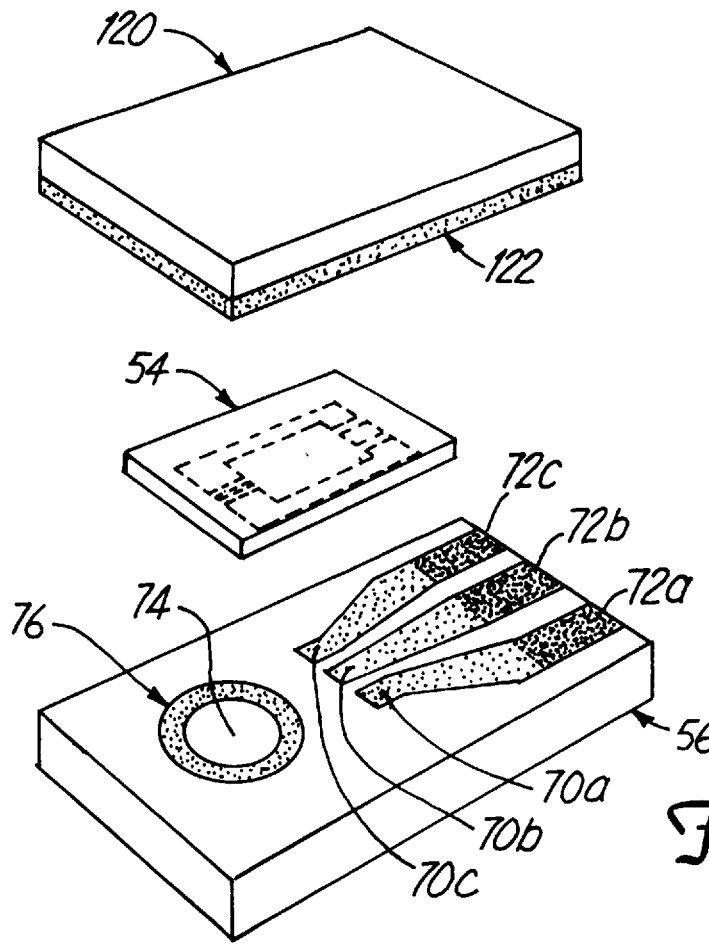
Figure 3C:
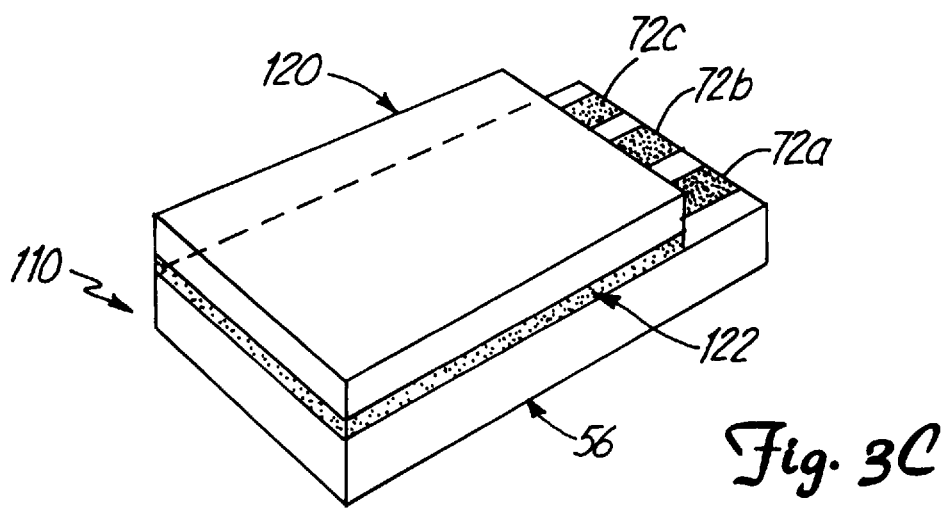

FIGS. 3A–3C illustrate an alternative ISFET sensor assembly 110 of the present invention in which a second substrate 120 is solder glass bonded to the first substrate 56, over the back of ISFET die 54 to form a hermetic seal about the die. The same reference numerals are used in FIGS. 3A–3C as were used in FIGS. 2A–2E for the same or similar components. As shown in FIG. 3A, a ring of solder glass 122 is applied around a periphery of surface 124 of second substrate 120. Second substrate 120 is then placed over ISFET die 54 on back surface 68 of substrate 56 and solder glass 120 is heated to bond second substrate 120 to first substrate 56. In an alternative embodiment, solder glass 122 is first bonded to substrate 56 and then bonded to substrate 120.

FIG. 3B is an exploded, perspective view of ISFET sensor assembly 110 as viewed from back surface 68 of substrate 56 as opposed to front surface 66. FIG. 3C shows ISFET sensor assembly 110 in an assembled state. The form, materials and fabrication of second substrate 120 can be varied in the same manner as was discussed with respect to substrate 56. The solder glass seal between substrates 56 and 120 can be replaced with condensation polymer, metal depositions, metals, alloys or polymers as desired for chemical resistance, structural support, insulation, surface bonding or vapor barrier properties that may be suitable for a particular application.

Figure 4A:
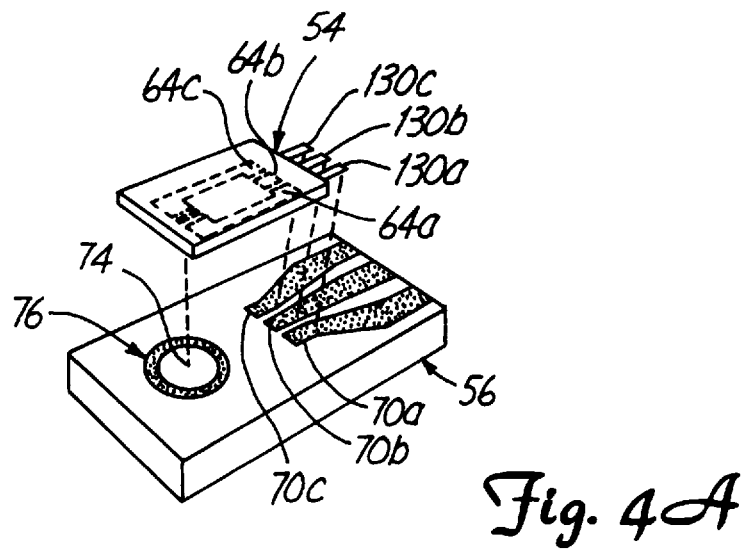
FIGS. 4A–4B and 5A–5B are perspective views of ISFET sensors having welded wire straps and welded wires, respectively, between an ISFET die and a substrate, according to alternative embodiments of the present invention.
Figure 4B:
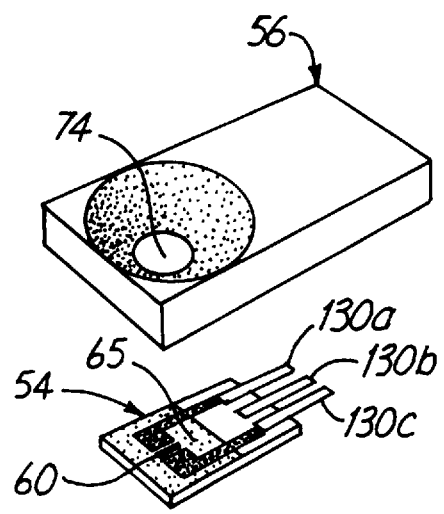
Figure 5A:
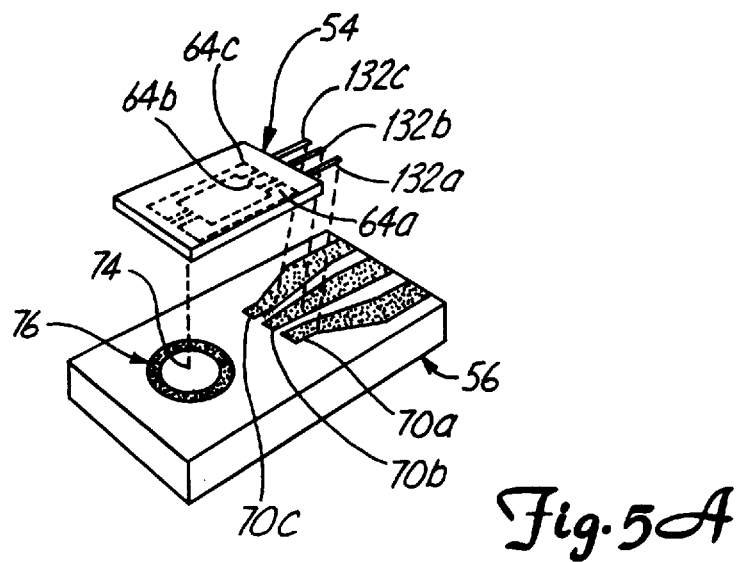
Figure 5B:
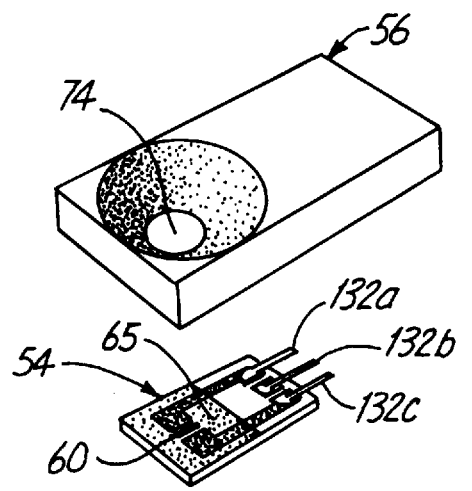

In FIGS. 4A and 4B, die bonding pads 64a–64c are electrically connected to substrate bonding pads 70a–70c with welded straps 130a–130c, rather that directly with solder or conductive adhesive, which allows the seal around substrate aperture 74 to be formed in a different assembly step and environment than the electrical connections. In FIGS. 5A and 5B, die bonding pads 64a–64c are electrically connected to substrate bonding pads 70a–70c with welded wires 132a–132c.

Figure 6A:
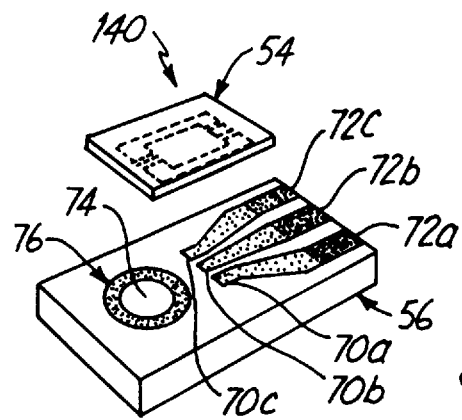
FIGS. 6A–6B are perspective views of an ISFET sensor having a two sealing rings according to an alternative embodiment of the present invention.
Figure 6B:
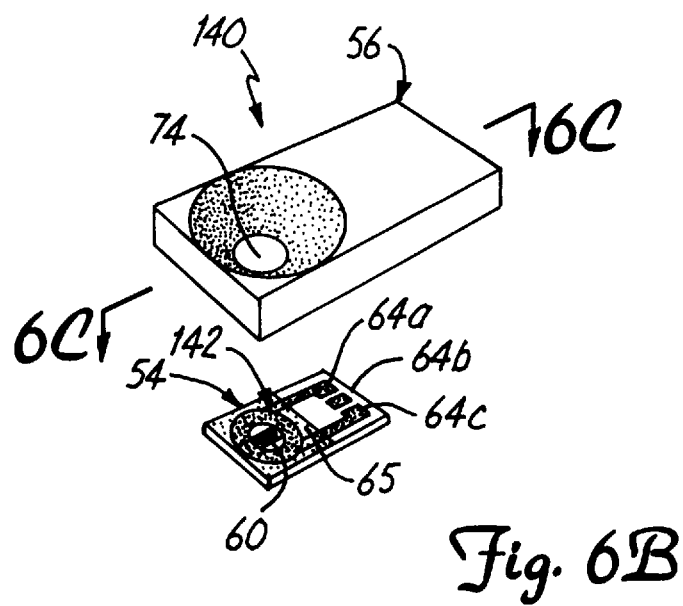

FIGS. 6A and 6B are perspective views of an ISFET sensor assembly 140 having two sealing rings, including substrate sealing ring 76 on substrate 56 and a corresponding ISFET die sealing ring 142 on ISFET die 54. ISFET die sealing ring 142 is applied over ion-sensitive membrane 65 and surrounds the ISFET gate region 60. In a preferred embodiment, sealing rings 76 and 142 include gold rings which are sealed together during assembly through thermal-pressure bonding. As discussed above, sealing rings 76 and 142 can include other metals, alloys, glasses or polymers as desired and can be bonded together through different methods. For example, a gold-tin or gold-silicon solder washer can be placed between sealing rings 76 and 142 and then heated to join the rings together.

Figure 6C:
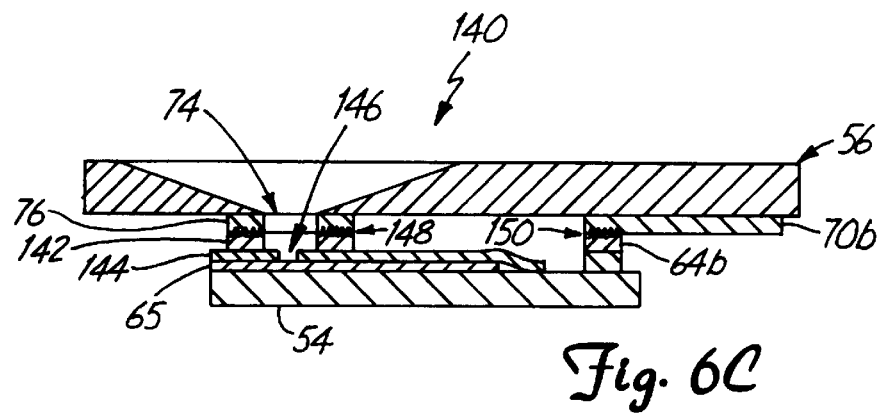
FIG. 6C is a cross sectional view of the ISFET sensor taken along lines 6C—6C of FIG. 6B.

FIG. 6C is a cross-sectional view of ISFET sensor assembly 140 as viewed along lines 6C—6C of FIG. 6B. Substrate 56 includes aperture 74 and carries sealing ring 76 and substrate bonding pad 70b. ISFET die 54 has several layers, including the ISFET structure itself, alumina ion-sensitive membrane 65 and platinum layer 144. Platinum layer 144 is applied over ion-sensitive membrane 65 and has an aperture 146 at the gate region of ISFET die 54 which exposes the ion-sensitive membrane to the sample solution entering substrate aperture 74. Sealing ring 142 is applied over platinum layer 144. Sealing ring 76 is bonded to sealing ring 142 through a gold thermal compression joint 148. Similarly, die bonding pads 64a–64c (only 64b is shown) are bonded to substrate bonding pads 70a–70c (only 70b is shown) with a gold thermal compression joint 150. Bonding pads 64a–64c and 70a–70c are preferably formed of gold. However, other sealing and bonding techniques may be used, as discussed above. Each layer of ISFET sensor assembly 140 acts as an adhesion promoter for the adjacent layers.

Figure 7:
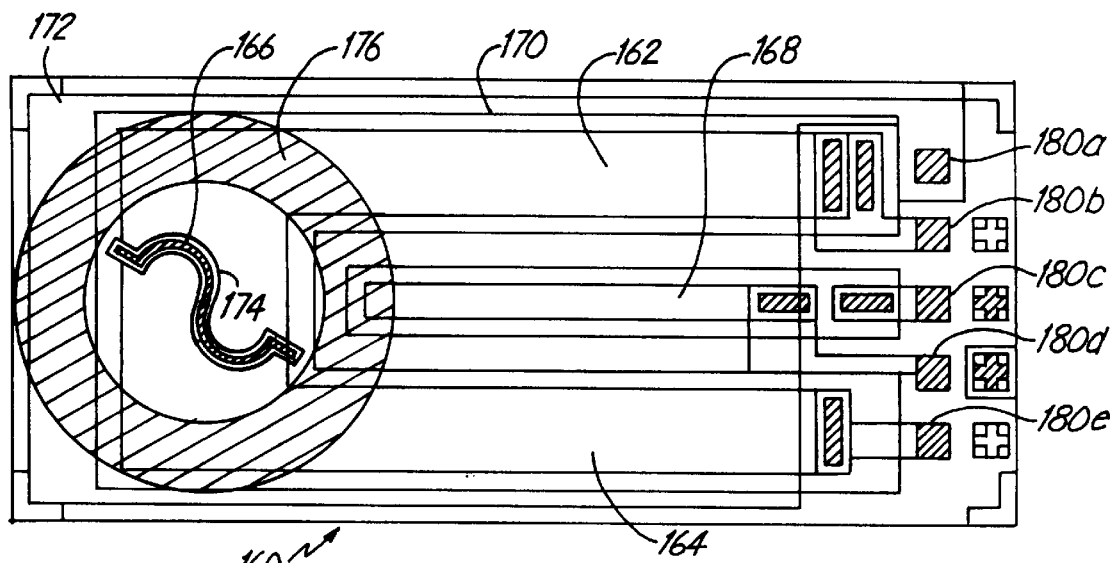
FIG. 7 is a top plan view of an ISFET die of the present invention in which the various layers of the die are shown superimposed on one another.

FIG. 7 is top plan view of an ISFET die 160 according to a preferred embodiment of the present invention, in which the various layers of material forming the die are superimposed on one another. Die 160 includes a source 162, a drain 164, a gate 166 and a temperature compensation diode 168. Gate 166 separates source 162 and drain 164. An ion-sensitive membrane 170 covers the gate region of ISFET die 160. Platinum layer 172 covers ion-sensitive membrane 170, except at an aperture 174 surrounding gate 166. A gold ring 176 is applied to platinum layer 172 around gate 166. Gate 166 has a generally sinusoidal or reverse-S shape which increases the effective width of gate 166 across source 162 and drain 164. This provides greater current drive capability for the ISFET and thus a greater sensitivity to changes in ion concentration of the sample solution. ISFET die 160 further includes a plurality of die bonding pads 180a–180e. Die bonding pad 180a is electrically coupled to platinum layer 172. Die bonding pad 180b is electrically coupled to source 162 and the semiconductor body of the source and drain. Die bonding pads 180c and 180d are electrically coupled to temperature compensation diode 168. Die bonding pad 180e is electrically coupled to drain 164.

Figure 8A:
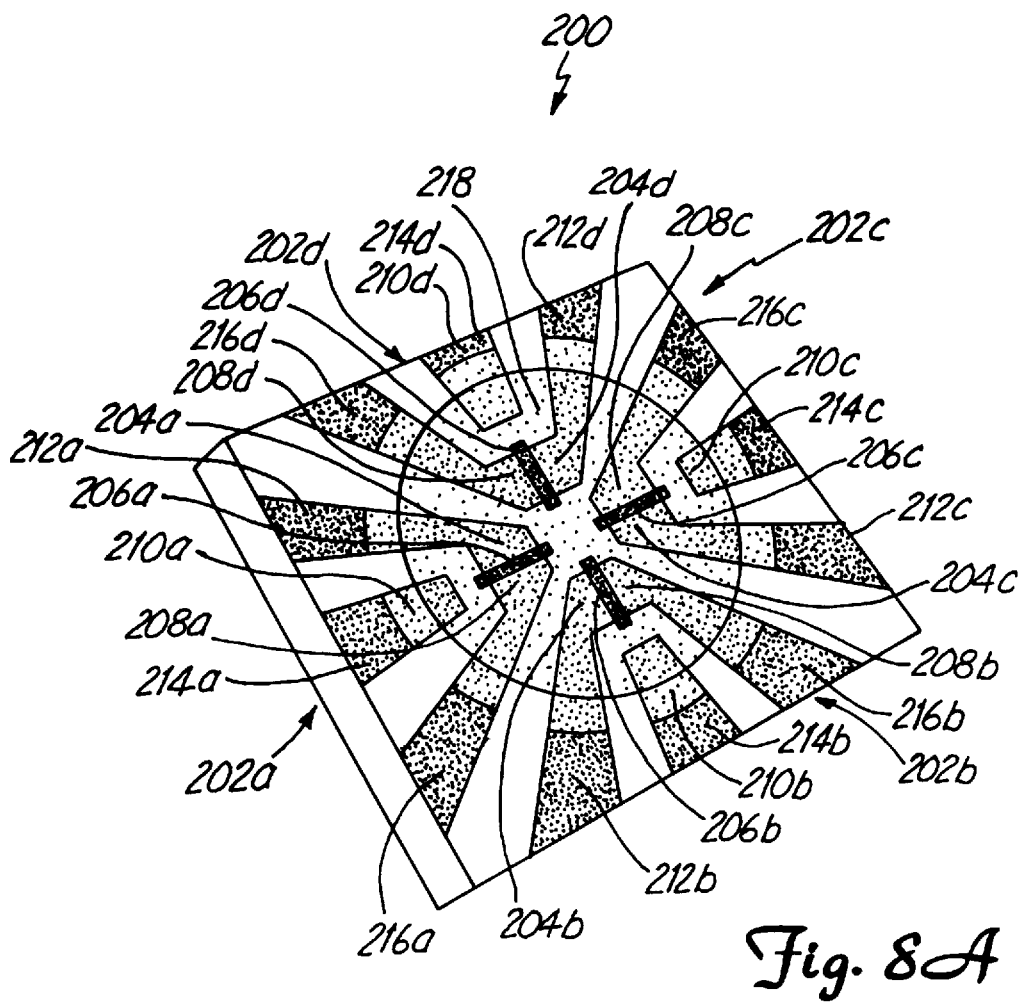
FIGS. 8A–8F are perspective views of a multiple, radially symmetrical ISFET sensor according to an alternative embodiment of the present invention.

FIGS. 8A–8F illustrate an ISFET sensor assembly having a radially symmetrical, multiple ISFET die according to an alternative embodiment of the present invention. In FIG. 8A, ISFET die 200 includes multiple ISFETs 202a, 202b, 202c and 202d. ISFET 202a includes source 204a, gate 206a, drain 208a, die substrate conductor 210a and die bonding pads 212a, 214a and 216a. ISFET 202b includes source 204b, gate 206b, drain 208b, die substrate conductor 210b and die bonding pads 212b, 214b and 216b. ISFET 202c includes source 204c, gate 206c, drain 208c, die substrate conductor 210c and die bonding pads 212c, 214c and 216c. ISFET 202d includes source 204d, gate 206d, drain 208d, die substrate conductor 210d and die bonding pads 212d, 214d and 216d. Ion-sensitive membrane 218 covers the gate, drain and source regions of ISFETs 202a–202d.

Figure 8D:
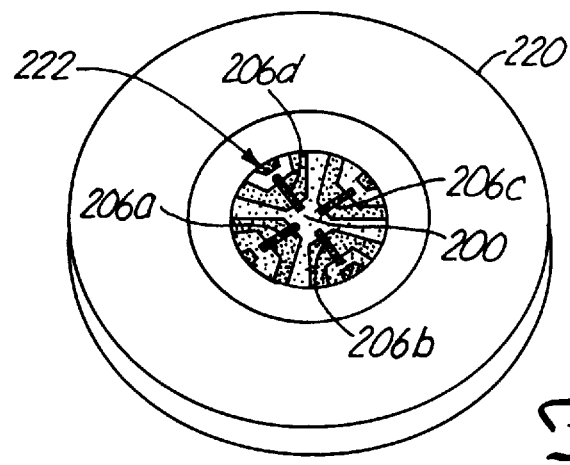
Figure 8C:
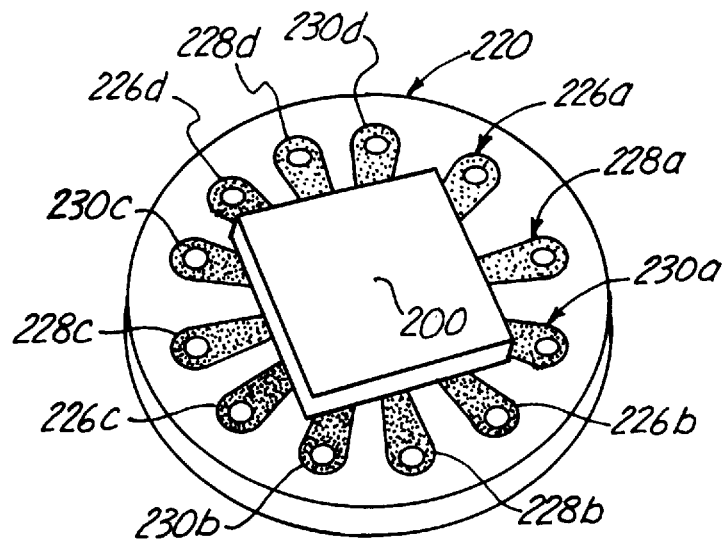
Figure 8B:
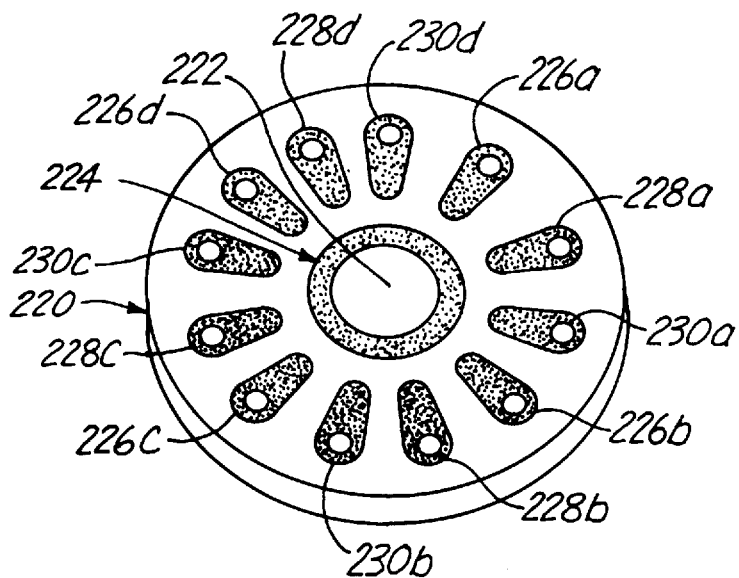

FIG. 8B is a perspective of view a back surface of a substrate 220 for mounting the multiple ISFET die 200 show in FIG. 8A. Substrate 220 includes substrate aperture 222, substrate sealing ring 224 and substrate bonding pads 226a–226d, 228a–228d and 230a–230d for electrically coupling to die bonding pads 212a–212d, 214a–214d and 216a–216d, respectively. FIG. 8C illustrates multiple ISFET die 200 bonded to substrate 220. FIG. 8D is perspective view of multiple ISFET die 200 and substrate 220, as viewed from a front surface of the substrate. Each gate region 206a–206d is exposed to the sample solution through substrate aperture 222.

Figure 8E:
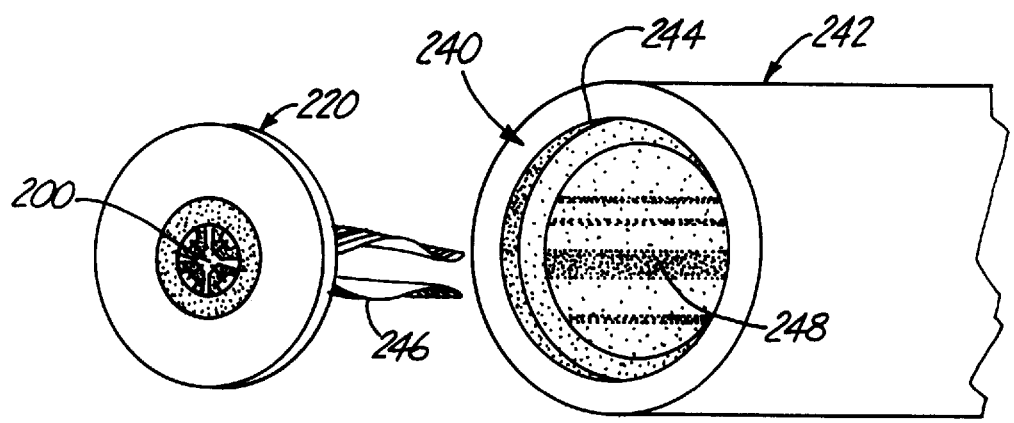
Figure 8F:
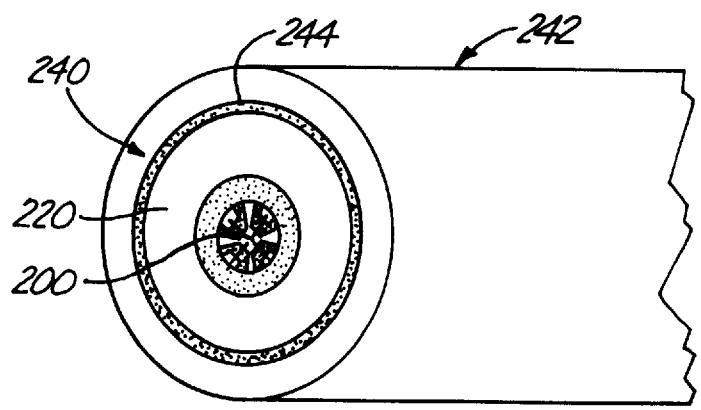

FIG. 8E is a perspective view illustrating the attachment of multiple ISFET die 200 and substrate 220 to a distal end 240 of a sensor housing or inner spindle body 242. Distal end 240 has a circular aperture 244 which receives substrate 220. One or more ribbon cables 246 are electrically coupled to substrate bonding pads 226a–226d, 228a–228d and 230a–230d (shown in FIG. 8B) and extend through an inner cavity 248 of sensor housing 242. Substrate 220 is sealed within aperture 244, as shown in FIG. 8F, by the sealing methods discussed with respect to the embodiment shown FIGS. 2A–2E.

Figure 9A:
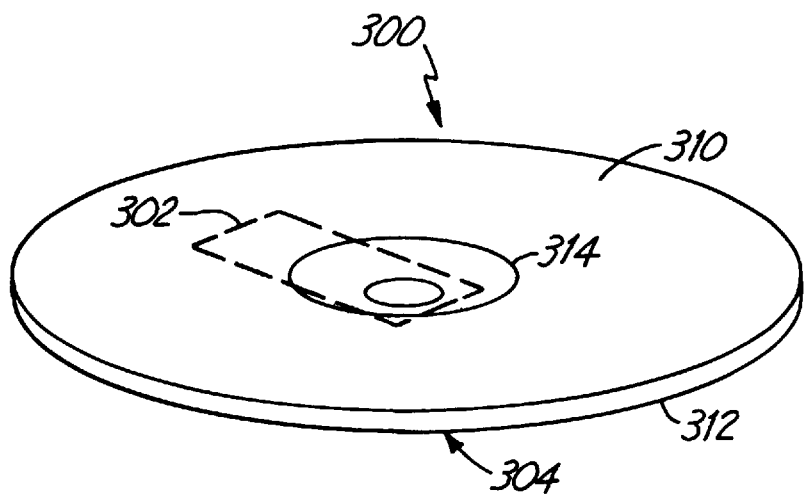
FIGS. 9A–9F are views of an ISFET sensor assembly according to another alternative embodiment of the present invention.
Figure 9B:
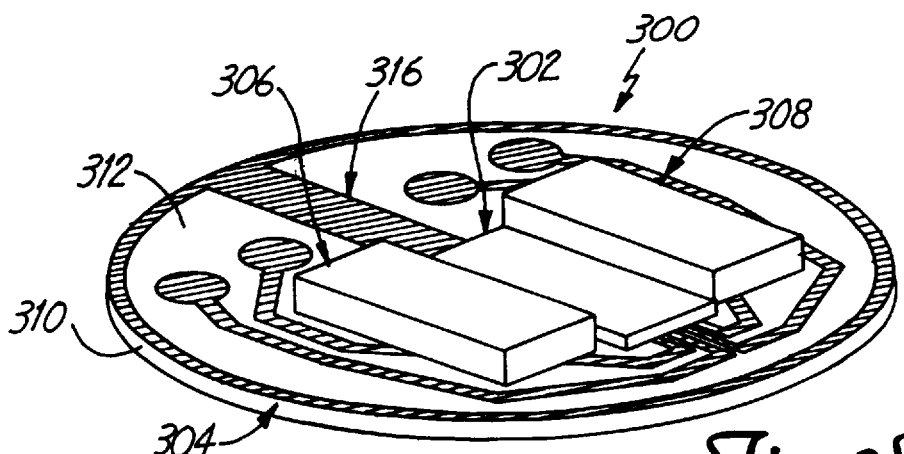

FIGS. 9A and 9B are perspective views illustrating opposite surfaces of an ISFET sensor assembly 300 according to another alternative embodiment of the present invention. ISFET sensor assembly 300 includes ISFET die 302, substrate 304 and metal oxide varistors (MOVs) 306 and 308. Substrate 304 has a front surface 310, a back surface 312 and an aperture 314. ISFET die 302 is attached to back surface 312 of substrate 304 such that its gate region is exposed through aperture 314. Back surface 312 includes conductive traces 316.

Figure 9C:
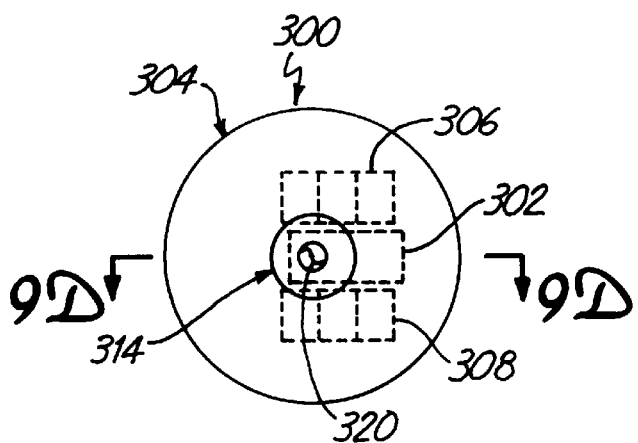
Figure 9D:

FIG. 9C is a top plan view of ISFET sensor assembly 300. ISFET die 302 and MOVs 306 and 308 are shown in phantom. Similar to the embodiment shown in FIG. 7, ISFET die 302 has a sinusoidal gate 320 which is exposed through aperture 314. FIG. 9D is cross section of substrate 304, as viewed along lines 9D—9D of FIG. 9C.

Figure 9E:
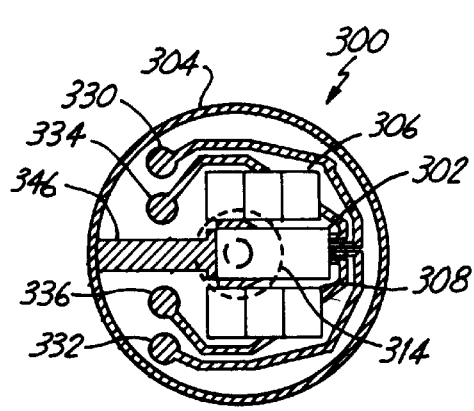
Figure 9F:
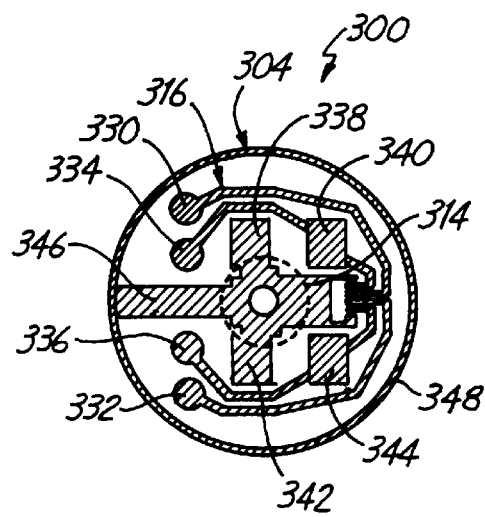

FIG. 9E is a bottom plan view of ISFET sensor assembly 300. FIG. 9F is a bottom plan view of substrate 304 with MOVs 306 and 308 and ISFET die 302 removed. Bonding pads 330 and 332 are electrically coupled to the temperature compensation diode on ISFET die 302. Bonding pads 334 and 336 are electrically coupled to the drain and source of the ISFET on ISFET die 302. Bonding pads 338 and 340 are electrically coupled to MOV 306, and bonding pads 342 and 344 are electrically coupled to MOV 308. Bonding pads 338 and 342 are electrically coupled to a guard 346 which is electrically coupled to a metallized ring 348 extending around the periphery of substrate 304. In a preferred embodiment, the conductive traces and bonding pads on substrate 304 are formed of gold.

Figure 10:
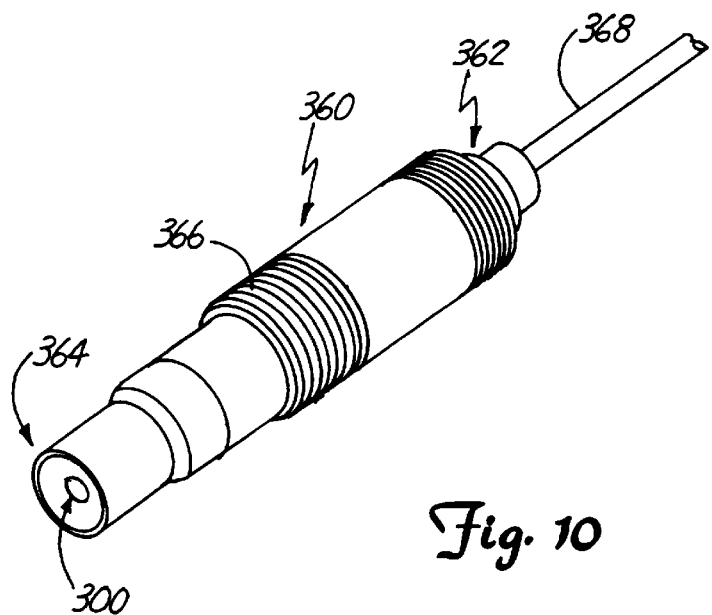
FIG. 10 is a perspective view of a sensor body for holding the ISFET sensor assembly shown in FIGS. 9A–9F.

FIG. 10 is a perspective view of a sensor body 360 for carrying the ISFET sensor assembly 300 shown in FIGS. 9A–9F. Sensor body 360 is a tubular body having a proximal end 362, a distal end 364 and an external screw thread 366 for securing the sensor body to a process. ISFET sensor assembly 300 is mounted within distal end 364 of sensor body 360, and a sensor cable 368 is attached to proximal end 362 for communicating with remote measurement or control circuitry.

Figure 11:
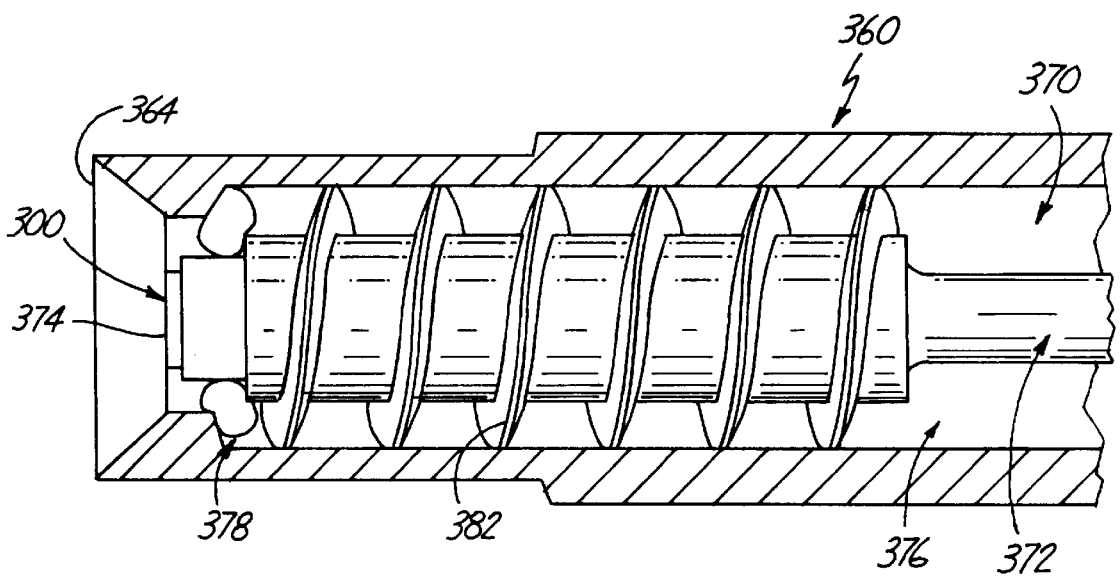
FIGS. 11 and 12 are cross sectional views of the sensor body shown in FIG. 10.

FIG. 11 is a partial, sectional view of the distal end 364 of sensor body 360. Sensor body 360 has an internal cavity 370 which carries an inner spindle body 372. ISFET sensor assembly 300 is mounted within a distal end of 374 of inner spindle body 372. ISFET sensor assembly 300 is exposed to the sample solution at distal end 374. A reference electrolyte 376 is contained within internal cavity 370. A rubber O-ring 378 forms a seal between inner spindle body 372 and sensor body 360 to seal internal cavity 370 from the sample solution. The walls of sensor body 360 are ionically permeable to allow a small amount of ionic communication between the sample solution and reference electrolyte 376.

Inner spindle body 372 includes a spiral junction 382 along its outer diameter which provides a long pathway to limit passage of poisoning ions from the sample solution to internal cavity 374. The structure and operation of the spiral junction 382 and the ionically permeable walls of sensor body 360 are described in greater detail in U.S. application Ser. No. 08/685,794, filed Jul. 24, 1996, and entitled "COMPOSITE CHANNEL JUNCTION," which is hereby incorporated by reference.

Figure 12:
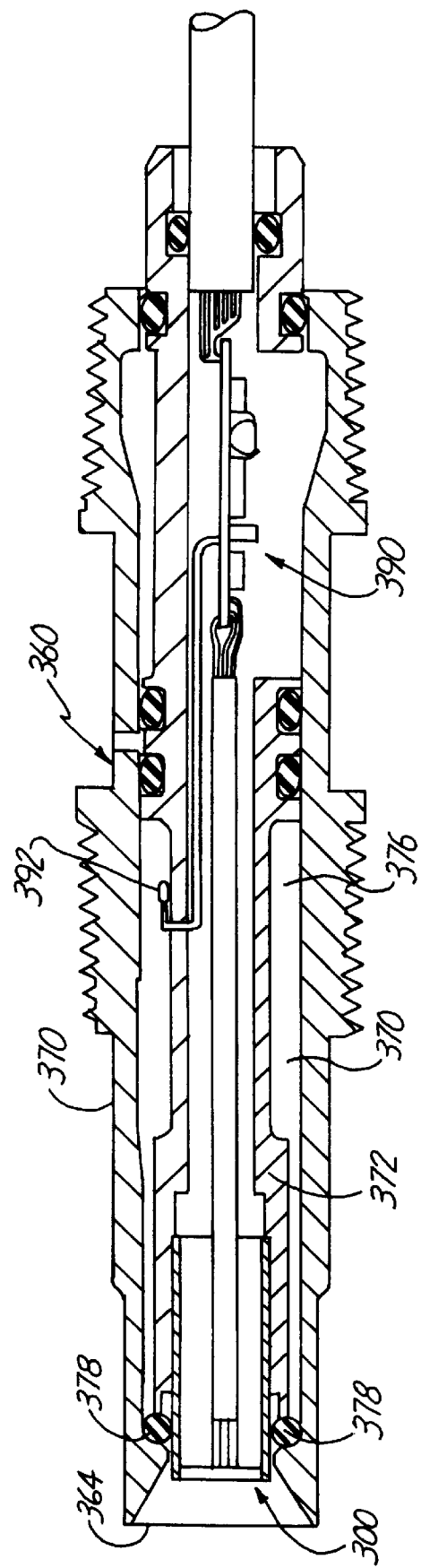

FIG. 12 is a more detailed cross sectional view of sensor body 360. ISFET 300 is electrically connected to a preamplifier printed circuit board 390 with wire leads extending through an inner lumen of spindle body 372. A reference electrode 392 extends from circuit board 390 to internal cavity 370 and is in contact with reference electrolyte 376 contained within the cavity.

CONCLUSION

The ISFET sensor of the present invention includes an ISFET die which is mounted to the back surface of a substrate which provides an impenetrable, abrasion resistant material over the entire ISFET die, except for the gate area. This limits damage from the solution to a thin band of material sealing the gate area from the rest of the ISFET die. Since the sealing material is positioned between the ISFET die and the substrate, the sealing material is well supported by the substrate such that it cannot lift from the ISFET die surface. Therefore, only solution which passes through to the die by permeation of and damage to the small area of sealing edge can attack the die. In addition, since the ion-sensitive surface of the ISFET die is bonded directly to the substrate, the corresponding die bonding pads abut the substrate bonding pads. As a result, wires are no longer required to be looped through the epoxy to make the electrical connections. This substantially reduces susceptibility to thermal expansion breakage.

The ISFET sensor of the present invention includes a gold thermal-pressure bond around the gate area, between the ISFET die and the substrate, which provides a stable, corrosion resistant, moisture barrier seal. Metallic solders, glasses or condensation polymer or metals could be substituted for the gold ring, as desired to in alternative embodiments. In addition, placing the substrate over the ISFET die provides intrinsic shielding from the abrasive action of the sample solution which flows along the thin ion-sensitive membrane at the gate region. These advantages greatly extend the operational life of the ISFET.

Although the present invention has been described with reference to preferred embodiments, workers skilled in the art will recognize that changes may be made in form and detail without departing from the spirit and scope of the invention.

What is claimed is:

1. An Ion-sensitive Field Effect Transistor (ISFET) sensor for sensing ion activity of a solution, the sensor comprising:
    a first substrate comprising a front surface exposed to the solution, a back surface opposite to the front surface and an aperture extending between the front and back surfaces;
    an ISFET semiconductor die comprising an ion-sensitive surface with a gate region, wherein the ion-sensitive surface is in substantially planar contact with and mounted to the back surface such that the gate region is exposed to the solution through the aperture; and
    a seal formed between the back surface of the first substrate and the ISFET semiconductor die and surrounding the aperture, which seals the die from the solution except at the gate region.

2. The ISFET sensor of claim 1 wherein:
    the first substrate further comprises a plurality of electrically conductive bonding pads on the back surface; and
    the ISFET semiconductor die further comprises a plurality of electrically conductive bonding pads on the ion-sensitive surface which abut and are electrically coupled to the plurality of electrically conductive bonding pads on the back surface of the first substrate.

3. The ISFET sensor of claim 1 wherein:
    the first substrate further comprises a plurality of electrically conductive bonding pads on the back surface;
    the ISFET semiconductor die further comprises a plurality of electrically conductive bonding pads on the ion-sensitive surface; and
    the ISFET sensor further comprises a plurality of electrically conductive leads having first ends attached to the plurality of electrically conductive bonding pads on the ion-sensitive surface and second ends which extend beyond a perimeter of the ISFET semiconductor die and are attached to the plurality of electrically conductive bonding pads on the back surface of the first substrate.

4. The ISFET sensor of claim 1 wherein the seal comprises a layer of polymer.

5. The ISFET sensor of claim 1 wherein the seal comprises a condensation polymer.

6. The ISFET sensor of claim 1 wherein the seal comprises a condensation metal.

7. The ISFET sensor of claim 1 wherein the seal comprises a metal selected from the group consisting of gold, platinum, nickel, titanium, tantalum and palladium silver.

8. The ISFET sensor of claim 1 wherein the seal is fabricated onto one of the back surface of the first substrate and the ion-sensitive surface of the ISFET die and then sealed to the other of the back surface of the first substrate and the ion-sensitive surface of the ISFET die.

9. The ISFET sensor of claim 1 wherein the seal comprises:
    a first metal seal attached to the back surface of the first substrate and surrounding the aperture;
    a second metal seal attached to the ion-sensitive surface of the ISFET semiconductor die and surrounding the gate region; and
    wherein the second metal seal is symmetrical with and bonded to the first metal seal.

10. The ISFET sensor of claim 9 wherein the first metal seal is thermal-pressure bonded to the second metal seal.

11. The ISFET sensor of claim 9 wherein the first metal seal is soldered to the second metal seal.

12. The ISFET sensor of claim 1 and further comprising:
    an ion-sensitive membrane formed on the ion-sensitive surface and covering the gate region;
    a layer of metal formed over the ion-sensitive surface and having an aperture along the gate region; and
    wherein the seal is attached to the layer of metal.

13. The ISFET sensor of claim 12 wherein the layer of metal comprises a material selected from the group consisting of gold, platinum, nickel, titanium, tantalum and palladium silver.

14. The ISFET sensor of claim 1 and further comprising:
    an ion-sensitive membrane formed on the ion-sensitive surface and covering the gate region; and
    a solution ground layer formed over the ion-sensitive membrane, extending within the aperture of the first substrate for contact with the solution and having an aperture along the gate region.

15. The ISFET sensor of claim 1 and further comprising:
    an ion-sensitive membrane formed on the ion-sensitive surface and covering the gate region; and
    a light blocking layer formed over the ion-sensitive membrane and having an aperture along the gate region.

16. The ISFET sensor of claim 1 and further comprising:
    an ion-sensitive membrane formed on the ion-sensitive surface and covering the gate region; and
    an oxide-reduction potential sensitive membrane formed over the ion-sensitive membrane, extending within the aperture of the first substrate for contact with the solution and having an aperture along the gate region.

17. The ISFET sensor of claim 1 and further comprising;
    a second substrate bonded to the back surface of the first substrate around a periphery of the TSFET semiconductor die such that the die is enclosed and sealed by the first and second substrates.

18. The ISFET sensor of claim 17 wherein the first and second substrates are bonded together with a condensation material.

19. The ISFET sensor of claim 1 and further comprising:

a sensor housing having an interior, an exterior and a housing aperture, wherein the first substrate is mounted to the sensor housing at the housing aperture such that the front surface faces the exterior and the back surface faces the interior.

20. The ISFET sensor of claim 19 wherein the first substrate is mounted to the sensor housing with a condensation material such that the ISFET semiconductor die is sealed within the interior of the sensor housing.

21. The ISFET sensor of claim 19 wherein:

the ISFET semiconductor die is mounted to the back surface of the first substrate with a condensation material, which seals the ISFET semiconductor die about the aperture in the first substrate; and the first substrate is mounted to the sensor housing with the condensation material.

22. The ISFET sensor of claim 19 wherein:

the sensor housing comprises a tube with a distal end;

the housing aperture is oriented in an axial direction at the distal end;

the first substrate has side walls which mate with the housing aperture; and the side walls of the first substrate are sealed to the housing aperture.

23. The ISFET sensor of claim 1 wherein the gate region has a sinusoidal shape.

24. The ISFET sensor of claim 1 wherein the ISFET semiconductor die comprises a plurality of ISFETs which are arranged on the die radially symmetrical to one another, each ISFET having a gate region which is exposed to the solution through the aperture.

25. An Ion-sensitive Field Effect Transistor (ISFET) sensor for sensing ion activity of a solution, the sensor comprising:

a first substrate comprising a front surface exposed to the solution, a back surface opposite to the front surface, an aperture extending between the front and back surfaces and a plurality of electrically conductive bonding pads on the back surface; and an ISFET semiconductor die comprising an ion-sensitive surface having a gate region and a plurality of electrically conductive bonding pads, wherein the ion-sensitive surface is mounted to and faces the back surface such that the gate region is exposed to the solution through the aperture and the bonding pads on the ion-sensitive surface are electrically coupled to the bonding pads on the back surface of the first substrate.

26. The ISFET sensor of claim 25 wherein the plurality of electrically conductive bonding pads on the ion-sensitive surface directly abut the plurality of electrically conductive bonding pads on the back surface of the first substrate.

27. The ISFET sensor of claim 25 wherein the ISFET sensor further comprises:

a plurality of electrically conductive leads having first ends attached to the plurality of electrically conductive bonding pads on the ion-sensitive surface and second ends which extend beyond a perimeter of the ISFET semiconductor die and are attached to the plurality of electrically conductive bonding pads on the back surface of the first substrate.

* * * * *

UNITED STATES PATENT AND TRADEMARK OFFICE
CERTIFICATE OF CORRECTION

PATENT NO. : 5,833,824
DATED : November 10, 1998
INVENTOR(S) : Barry W. Benton

It is certified that error appears in the above-indentified patent and that said Letters Patent is hereby corrected as shown below:

Column 10, line 4, delete "condensation".

Column 10, line 6, delete "condensation".

Signed and Sealed this

First Day of June, 1999

Attest:

Q. TODD DICKINSON

*Attesting Officer*     *Acting Commissioner of Patents and Trademarks*